United States Patent [19]
Hoffmann et al.

[11] Patent Number: 5,542,542
[45] Date of Patent: Aug. 6, 1996

[54] SYSTEM FOR DETECTING CONTAMINANTS

[75] Inventors: John D. Hoffmann, Burnaby; Robert W. Gooding, Vancouver; Norman Roberts, Burnaby; Robert S. Hart, Salmon Arm, all of Canada

[73] Assignee: Pulp and Paper Research Institute of Canada, Pointe Claire, Canada

[21] Appl. No.: 351,639

[22] Filed: Dec. 7, 1994

[51] Int. Cl.$^6$ .................. B03B 7/00; D21C 7/14
[52] U.S. Cl. .............. 209/17; 209/273; 209/306; 162/49; 162/55; 162/263
[58] Field of Search .................. 209/12.1, 17, 273, 209/281, 283, 305, 306, 725; 162/4, 48, 49, 55, 263, 272; 210/96.1, 739, 787, 806

[56] References Cited

U.S. PATENT DOCUMENTS

| | | | |
|---|---|---|---|
| 3,709,614 | 1/1973 | Hayakawa | 73/865.5 X |
| 3,912,622 | 10/1975 | Bolton et al. | 209/17 |
| 3,964,996 | 6/1976 | Holz et al. | 209/273 X |
| 4,252,640 | 2/1981 | Musselmann | 209/17 |
| 4,301,000 | 11/1981 | Rankin | 209/17 |
| 4,443,331 | 4/1984 | Amand | 209/725 X |
| 4,620,671 | 11/1986 | Skaar | 209/17 X |
| 4,646,979 | 3/1987 | Musselmann et al. | 209/273 X |
| 4,726,880 | 2/1988 | Smith | 162/4 |
| 4,758,308 | 7/1988 | Carr | 162/49 X |
| 5,000,842 | 3/1991 | Ljokkoi | 209/306 X |
| 5,405,499 | 4/1995 | Vinson | 162/55 X |

FOREIGN PATENT DOCUMENTS 2061133 5/1981 United Kingdom .................. 209/17

OTHER PUBLICATIONS

The Globe and Mail, "Plastic Places Paper Sales at Risk", Apr. 14, 1984.
Pulp and Paper Journal, Jan. 1984, vol. 37, No. 1, "Plastic Contamination Costing Pulp Mills Dearly", Bob Westergaard.
Pulp & Paper Canada 89:1 (1988), "Plastic Contamination in the Pulp Mill: An Overview", M. A. Robitaille.
Pulp & Paper, Jun. 1990, "New Lightweight Cleaner Units Solve Mill's Plastic Problems", Michel Marson.
Light Weight Cotaminant Monitoring System, Gadget #16, St. Anne–Nackawic Pulp Company Ltd., M. A. Robitaille.

*Primary Examiner*—William E. Terrell
*Assistant Examiner*—Tuan N. Nguyen
*Attorney, Agent, or Firm*—Swabey Ogilvy Renault

[57] ABSTRACT

A method and apparatus are described for continuously sampling a process stream, or reservoir of aqueous cellulosic pulp and detecting oversize contaminants in the sampled stream. This serves the overall objective of estimating the level of contamination in the process stream or reservoir during a given period of production; the method may include the following stages: 1) a continuous sample stream is drawn from the process or main stream, 2) the stream is passed through a centrifugal device which divides the sampled stream according to density, 3) the stream with the higher level of contaminants from the centrifugal device is passed to a screen which isolates the contaminants, and 4) the contaminants are flushed from the screen so that they can be quantified; these measurements are used to assess the purity of the material being produced. One useful application of this invention is to assess the presence of trace amounts of plastic contaminants in the production of the cellulosic pulp. Compared to manual methods for inspecting for plastic, this invention provides a measurement which is more accurate, more convenient, and less subjective.

13 Claims, 3 Drawing Sheets

FIG. 1

FIG_4

FIG_5

SYSTEM FOR DETECTING CONTAMINANTS

BACKGROUND OF THE INVENTION i) Field of the Invention

This invention relates to contaminant detection in paper pulp, and particularly to a device for detecting and measuring the concentration of lightweight, oversize contaminant particles in virgin pulp and recycled pulp. The invention also relates to an apparatus for separating the lightweight contaminants from pulp and isolating the lightweight, oversize contaminants.

ii) Description of Prior Art

In the manufacture of paper products, an appropriate fibre pulp is used which may be purchased in the form of solid pulp sheets, or processed in liquid form. It has long been known that the resulting paper products are greatly affected by the inclusion of foreign matter in the basic pulp from which the paper product is made. Common contaminants such as dirt, pitch, fibre bundles (identified in the art as shives), and the like are the usual contaminants encountered in virgin pulp. Various means have been provided for the detection of these contaminants.

Certain contaminants, such as lightweight plastic, can cause serious problems in the production of various grades of paper at much lower concentrations than common contaminants. See, for example, Enchin H. "Plastic Places Paper Sales at Risk", The Globe and Mail (1994 Apr. 14), p. B5, Westergaard B., "Plastic Contamination Costing Pulp Mills Dearly", Pulp and Paper J. 37(1):74–78, (1984); and Robitaille M. "Plastic Contamination in the Pulp Mill: an Overview", Pulp and Paper Can. 89(1):121–125 (1988). In the production of coated paper, for example, a blade spreads the coating medium over a fast-moving, continuous paper sheet. A plastic speck protruding from the surface of the sheet can catch on the blade and obstruct the flow of the coating medium. A streak of uncoated paper will result and the entire reel of paper will be rejected. The speck can also cause the sheet to tear, and lost production will result. In other paper grades, plastic specks can interfere with the transfer of ink or surface treatments to the paper. In tissue manufacture, plastic specks can stick to the highly-polished dryer cylinder and cause sheet tears.

An accurate and convenient method is required to inspect the pulp for plastic specks before it is made into paper. Contaminated pulp can then be redirected for use in paper grades which are not sensitive to plastic contaminants. Accurate measurements of plastic levels are also useful in identifying operating procedures or equipment which reduce the level of contamination- The measurements can also give an early warning of any process upsets or equipment failures which have caused contaminant levels to increase.

The most commonly used method for measuring plastic levels is the inspection of dried pulp sheets. This is the form the pulp is typically in when it leaves the pulp mill to go to the paper mill. The sheet inspection procedure is manual and uses transmitted and/or reflected light. The pulp sheet may be wetted to make the pulp more transparent. There are, however, serious flaws with this method: 1) it is subjective, 2) clear and white plastic specks are difficult to see against the white pulp background, and 3) the amount of pulp inspected is too small to give a statistically sound measurement of plastic contaminants.

Some other measurement techniques are based on intermittently sampling a small amount of the pulp while it is in aqueous suspension, and manually passing the suspension through a lab-type pulp screen, such as the Somerville Fractionator, Pulmac Shive Analyzer or Valley Flat Screen. This approach is more flexible, inasmuch as the pulp samples may be taken at various points in the process, either at the pulp mill or paper mill, but it has drawbacks that make it less attractive than the sheet-inspection procedure described above: 1) It is less convenient because the sample must be brought to a lab to be analyzed. 2) Considerable amounts of pulp fibre may be retained on the screen with the plastic contaminants. The pulp must therefore be dissolved using a chemical treatment, or the specks must be isolated manually. 3) Most seriously, the amount of pulp sampled is less than that obtained in the sheet-inspection approach, which is already too little to give a statistically sound measurement.

Several methods have been developed which sample the pulp suspensions in sufficient quantities to give a statistically sound measurement of plastic contaminants, but they have found only limited use. One is the Gyroclean (Trade Mark) which is a device that concentrates lightweight contaminants using a centrifuge with continuous flow-through. (See, for example, Marson M. "New Lightweight Concentrator Units Solve Mill's Plastic Problems", Pulp and Paper 93–96 (June 1990); and Julien Saint Amand J. "Process and Device for Separating Particles in a Fluid Especially for the Cleaning of the Suspensions Handled in the Paper Industry", U.S. Pat. No. 4,443,331 (1994)). One limitation of this approach is that this equipment is very costly to purchase and maintain. Another problem is that the incomplete separation of fibre and plastic contaminants will require that the sample be brought to the lab for additional treatments to isolate the plastic specks.

Another method for measuring plastic contamination of pulp is described by Robitaille M.A., Peeling D.A. "Light Weight Contaminant Monitoring System", 1987, CPPA Gadget Competition p.59–61. With this approach, a continuous stream of pulp is sampled from the process line and passed through a centrifugal device to concentrate the lightweight plastic particles. The stream with lightweight particles then passes to a settling tank. Lightweight plastic specks are intended to float to the surface of the tank, where they can be skimmed off to give a measure of plastic contamination levels. There are two main problems with this approach. First, the buoyant forces of certain plastic specks may be too small to allow the floatation cell to work efficiently and these specks will not be collected by the floatation cell. Second, the surface of the floatation tank may be obscured by steam, foam and pulp, and the collection of isolated plastic specks will become very difficult.

The contaminant detection method of Carr W. F. "System for Monitoring Contaminants with a detector in a Paper Pulp System", U.S. Pat. No. 4,758,308 (1988), is similar to that described above inasmuch as a continuously sampled stream of pulp is removed from the process stream, and passed through a centrifugal device to concentrate the contaminants. It differs, however, inasmuch as the contaminants are quantified not by isolating them for manual inspection, but by passing a dilute suspension of the contaminants past an electronic camera. The camera images can be analyzed to produce an electronic signal that indicates the level of contamination in the suspension. The problem with this approach, however, is that light imaging of the contaminants would not be expected to distinguish between plastic contaminants and other, more common, but less harmful contaminants. Plastic contaminants exist at much lower concentrations than pitch, shives, talc balls, and other common contaminants. Conclusive identification of plastic requires off-line inspection. Collection of the plastic specks also offers the advantage of being able to archive specks for further analysis and comparison.

The detection apparatus of Hayakawa, U.S. Pat. No. 3,709,614 is like that of Carr above inasmuch as contaminants are concentrated from a flowing suspension and passed to an inspection cell where an electronic camera assesses the contaminant concentration. The principal difference is in the use of screens instead of centrifugal devices to concentrate the contaminants. The use of the electronic camera, however, leads this apparatus to share the limitations which were identified with the detection method of Carr.

There is thus a very significant demand in the art for a method and device for detecting and measuring contaminant particles, particularly lightweight plastic particles. The system should preferably sample the pulp continuously to provide a large and representative pulp sample. It should efficiently remove and isolate the specks for quantification and analysis, be of low cost, and provide a convenient and quick measurement of contaminant concentration.

SUMMARY OF THE INVENTION

The present invention provides an apparatus and method for rapidly and conveniently isolating oversize contaminants from a flowing pulp suspension. This invention can thus be used to measure the degree of contamination in the pulp suspension, and to provide an evaluation of the level of contamination in the pulp suspension from which the stream was sampled.

An object of the invention is to provide an analytic screen which isolates oversize contaminants from a flowing pulp suspension so that these contaminants can be counted and analyzed.

A further object of the invention is to provide an analytic screen which retains the oversize contaminants, as described above, but does not cause the contaminants to be comminuted or appreciably altered in shape.

Still another object of the invention is to provide an analytic screen which retains oversize contaminants, as described above and which resists plugging of the apertures of the screen with pulp. Desirably the screen avoids the formation of fibre flocs or strings which could also block the screen apertures. In this way reliable operation of the invention is achieved, which is very important for its application as a device for the analysis of a continuous sample from a main process stream.

Yet another object of the invention is to provide an analytic screen which retains oversize contaminants, as described above, but which permits ready passage of the fibres through the screen apertures. It is important to minimize the accumulation of fibre within the screen so that the captured contaminants are not obscured by retained pulp fibres. Minimizing the amount of retained pulp is very important for facilitating the evaluation of the retained contaminants, and ensuring the convenient and rapid measurement of the retained contaminants.

A further object of the invention is to provide an analytic screen which retains oversize contaminants, as described above, from which the contaminants can be purged on an intermittent basis. This is very important to ensure that the contaminants are presented for inspection in a convenient manner.

A still further object of the invention is to provide a suitable hydraulic system for sampling a continuous flow from a process stream, or from a suspension in a vessel being analyzed off-line. This hydraulic system will include the required piping for obtaining a representative sample from the process stream or vessel and for disposing of the suspension after analysis. It may also include a centrifugal device for concentrating contaminants of specific density ranges from the suspension, before the suspension with the concentrated levels of contaminants is presented to the analytic screen.

Still further the invention provides a process for evaluating the contaminant content of a paper pulp, and especially the concentration of lightweight, oversize plastic contaminant particles.

Thus in accordance with one aspect of the invention there is provided a process for determining the contaminant content of an aqueous cellulosic pulp comprising: a) withdrawing a sample stream of aqueous cellulosic pulp from a mass of said pulp, b) separating a contaminant fraction from a pulp fibre fraction, of said pulp, c) screening oversize contaminants in said contaminant fraction with a screen, while preventing blockage of the screen with pulp fibers and oversize contaminants of the contaminant fraction, and maintaining said contaminants in a zone adjacent said screen, said screen having apertures of a size such as to be a barrier to passage of the oversize contaminants while permitting passage of an aqueous vehicle and residual pulp fibers of said contaminant fraction, d) recovering the oversize contaminants substantially free of pulp fibres, from said zone, e) measuring the recovered oversized contaminants, and f) determining the contaminant content of said pulp from the measurement of e) in conjunction with operating parameters of steps a), b) and c).

In another aspect of the invention there is provided an apparatus for use in determining the contaminant content of an aqueous cellulosic pulp comprising: i) a separating unit for separating a sample stream of an aqueous cellulosic pulp into a contaminant fraction and a fibre fraction; said separating unit having an inlet for flow into the unit of the sample stream, a first outlet for the fibre fraction and a second outlet for the contaminant fraction, ii) a screening unit in flow communication with said second outlet via a first line, and including a screen and means to induce pressure pulsations in a zone adjacent said screen effective to prevent blockage of the screen, and maintain the contaminants in said zone, said screen having apertures of a size such as to be a barrier to passage of oversize contaminants in the contaminant fraction while permitting passage of an aqueous vehicle and residual pulp fibres of the contaminant fraction, iii) a flushing line communicating with said screening unit for flow of flushing liquid to said zone, iv) a second line in flow communication with said screening unit for flow of flushing liquid with oversize contaminants from said screening unit, v) a collecting unit for contaminants in flow communication with said zone, vi) a first valve associated with said first line adjustable between open and closed positions to allow and prevent flow of the contaminant fraction from said separating unit to said screening unit, vii) a second valve associated with said flushing line adjustable between open and closed positions to allow and prevent flow of flushing liquid to said screening unit, and viii) a third valve associated with said second line adjustable between open and closed positions to allow and prevent flow of flushing liquid and contaminants from said zone of said screening unit to said collecting unit.

In still another aspect of the invention there is provided a screen device for separating, collecting or isolating oversize contaminants in an aqueous cellulosic pulp comprising: i) a housing having a first inlet port for flow of contaminant fraction of the cellulosic pulp, ii) a screen in said housing, said screen having apertures of a size such as to be a barrier to passage of oversize contaminants in the contaminant fraction while permitting passage of an aqueous vehicle and residual pulp fibres of the contaminant fraction, iii) means in said housing to induce pressure pulsations effective to prevent blockage of said screen, and maintain said contaminants in a zone between said screen and said means, iv) a first outlet port in said housing for passage of aqueous vehicle and residual pulp fibres downstream of the screen, v) a second inlet port in said housing for entry of flushing liquid to remove the contaminants from said zone, and vi) a second outlet port for flow of flushing liquid and removed contaminants from said housing.

DESCRIPTION OF PREFERRED EMBODIMENT i) Process

The sample stream may suitably be derived from a process stream of the aqueous pulp such process stream being developed at the site of pulp manufacture. In such case tile sample stream is bled from the process stream as the main stream without interruption of the main stream, and is representative of the composition of such main stream.

Suitably the sample stream is withdrawn in step a) as a continuous flow stream and the aqueous fibre fraction of the stream formed during the separating step and the aqueous vehicle with residual pulp fibres derived from the contaminant fraction are recycled continuously to the main stream to prevent loss of pulp fibres.

The sample stream may also be withdrawn from a vessel or reservoir housing the aqueous pulp.

The separating step b) is suitably carried out by continuously centrifuging a continuous sample stream to produce the pulp fibre fraction and the contaminant fraction with continuous discharge of the fibre fraction, and preferably its recycling to the main stream, and continuous feeding of the contaminant function to the screen in step c).

As described more fully hereinbelow, the continuous process is preferably operated with a detection mode, a flush mode and a collection mode. During the flush mode and the collection mode, feeding of the contaminant fraction to the screen is interrupted and the contaminant fraction is discharged from the centrifuge, suitably with the fibre fraction. Hence the contaminant fraction is discharged continuously from the centrifuge but only continually to the screen.

After et measured time period to allow collection of oversize contaminants in a collection zone, feeding of the contaminant fraction to the screen in the detection mode is interrupted and the screen is flushed, suitably with water, in a flushing mode and the flushings are discharged from the screen unit, and suitably may be recycled to the main stream. The purpose of the flushing mode is to remove residual fibres through the screen so that the collection zone contains a high content of collected contaminants and is substantially free of pulp fibres which would interfere with the measurement in the collection mode.

The collection zone is located adjacent the screen and is sometimes referred to herein as the zone adjacent the screen.

In the collection mode the discharge line for the flushings is closed and a collector line is opened to allow for flushing liquid to wash the contaminants from the collection zone and deliver them to a collector unit.

The contaminants are recovered in the collector from the flushing liquid and measured by some convenient parameter, for example, counting the contaminant specks or by weight.

In order to determine the contaminant content of the main stream this measurement is related to other operating parameters of the process so that a meaningful relationship is derived from the measurement of the collected contaminants and parameters of the sample stream from which the contaminants were removed.

The process has particular application to the determination of the content of plastic particles in the pulp.

ii) Apparatus

The apparatus of the invention particularly includes a separating unit and a screening unit which operate for delivery of the oversize contaminants to a collector unit where measurement of the contaminants is carried out.

The separating unit is suitably a centrifugal separator which separates the sample stream, preferably on a continuous basis, according to density of the components of pulp, and, in particular separates the sample into a contaminant fraction and a pulp fibre fraction.

The screening unit in particular is a screen device which suitably comprises a rotor and the screen comprises a cylindrical tubular wall having the apertures therein; the rotor being disposed in spaced apart relationship with the tubular wall. An outlet in the screening unit is in flow communication with the downstream side of the screen, for discharge of liquid and residual pulp fibres passing through the screen.

The rotor suitably has a cylindrical body and appendages or protuberances on the surface of the body which, during rotation of the rotor, induce pressure pulsations at the tubular wall. These pulsations serve to produce short backflows of liquid and fibres passing through the screen during the detection and flushing modes and thus prevent blockage of the screen by pulp fibers and contaminants.

In particular the pulsations maintain the contaminants in an annular collection zone of the screening unit between the rotor and the screen. The concentration of contaminants in this annular zone increases throughout the detection mode.

Conveniently the apparatus includes a second flushing line communicating with the screening unit, and a valve associated with this second flushing line, the valve being adjustable between open and closed positions to permit flow of flushing liquid into the screening unit during the flushing mode.

As indicated above the flushing mode serves to remove residual fibres from the annular zone prior to the collection mode so that the annular zone has a high content of contaminants and is substantially free of fibres at the commencement of the collection mode.

Thus the apparatus of the invention includes an analytic screen which is itself an aspect of the invention in conjunction with a hydraulic system.

The analytic screen for retaining the oversize contaminants may particularly comprise: 1) at least one inlet for the sample flow to enter with the contaminant fractions, 2) a screen in the form of a screen plate with apertures through which fluid and pulp fibres pass, but which retains or prevents passage of the oversize contaminants, 3) a rotor which induces pressure pulsations to backflush the screen plate apertures and prevents the screen plate apertures from plugging with pulp fibers or contaminants, 4) an outlet for transporting the water and fibre that has passed through the screen plate and from the analytic screen for disposal, and 5) a purge or flush system which can be intermittently operated to flush oversize contaminants that have been retained by the screen plate to a separate collection container. The analytic screen is typically enclosed to prevent extraneous contaminants (i.e. contaminants not from the sample process stream) from entering the analytic screen. An enclosed construction also prevents screen overflows and the loss of the collected contaminants. The analytic screen may also be pressurized to enhance the pulsation effect of the rotor.

The hydraulic system comprises the piping, conduits or lines required to draw a representative sample from a process line, or from a vessel containing a pulp suspension, and to deliver the suspension to the analytic screen. It also includes the piping required to take the screened suspension from the screen. The hydraulic system may include the centrifugal device for concentrating contaminants of specific densities before presenting the concentrated stream of contaminants to the analytic screen. The hydraulic system may also include the required valves and instrumentation to establish the appropriate pressures and flows for efficient operation of the analytic screen and centrifugal device.

The present invention would typically be used on-line to assess the level of contaminants in the process stream. It could be used off-line in a mill quality control department or testing laboratory to determine the level of contaminants in a suspension of pulp. From this measurement, the mill could determine the level of contamination in a particular shipment of pulp, or assess the effectiveness of some change in the raw material supply or mill process which reduces contamination. Certain contaminants can have a very damaging impact on the ability to make certain grades of paper, and on the quality of the paper. It is important to detect the highly contaminated pulp so that 1) this pulp is not used for the type of product where the contaminant will cause difficulties, and 2) corrective actions can be taken to eliminate the contaminants from the pulp. While methods exist to detect and differentiate between different contaminants, the present invention is unique in that it is able to quickly and efficiently sample a sufficiently large quantity of pulp, and then to isolate the contaminants so that the level of contamination can be estimated and a positive identification can be made of the type of contaminant.

Other objects, purposes and advantages of the invention will be apparent from consideration of the following description.

BRIEF DESCRIPTION OF THE DRAWINGS

The invention is illustrated in particular and preferred embodiments by reference to the accompanying drawing in which.

DETAILED DESCRIPTION OF THE PREFERRED EMBODIMENTS OF THE INVENTION WITH REFERENCE TO THE DRAWINGS

Figure 1:
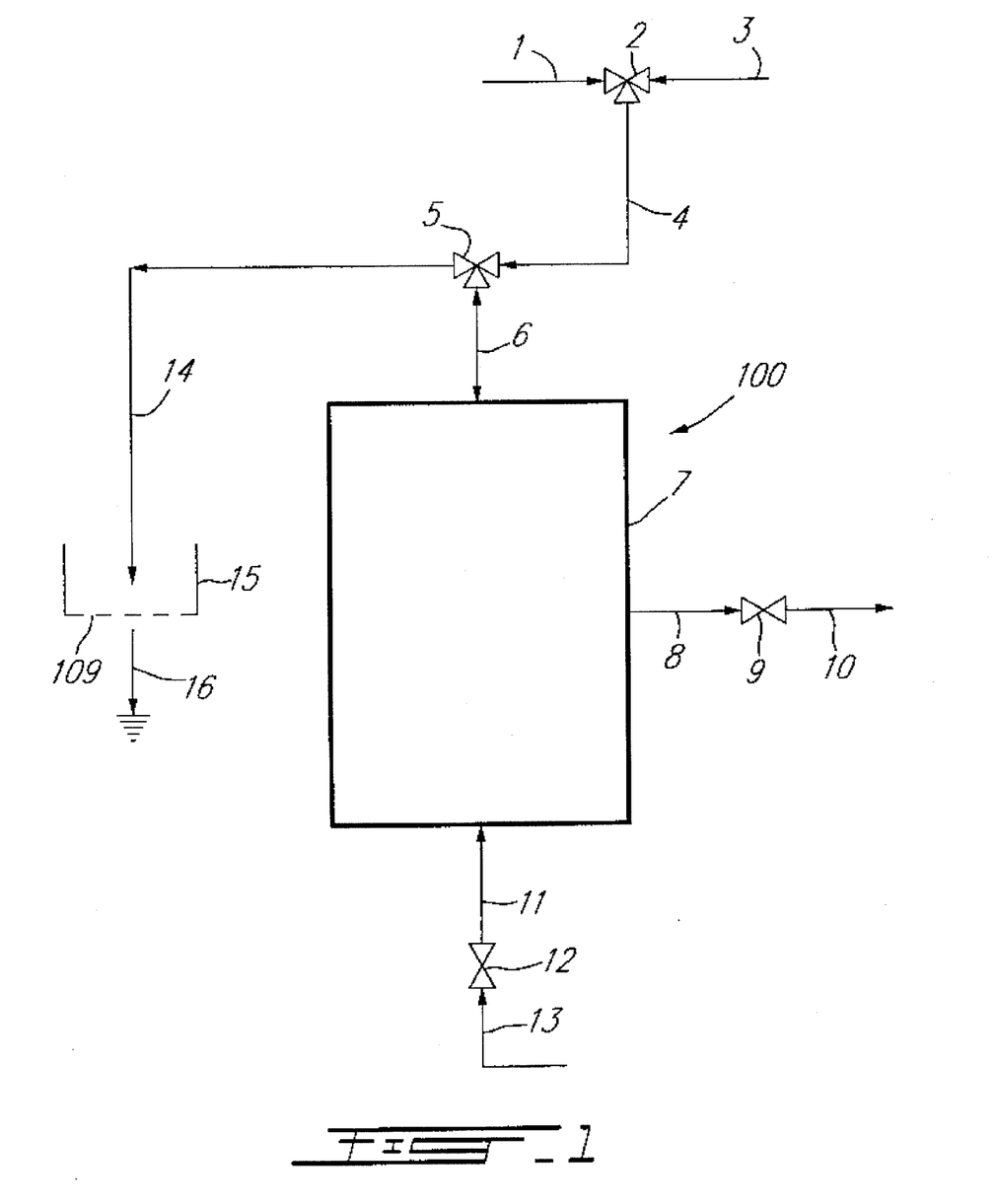
FIG. 1 is a schematic elevation view of an embodiment of an analytic screen device according to the invention, showing the placement of the inlet and outlet fittings along with the systems for purging and collecting the contaminants.
Figure 2:
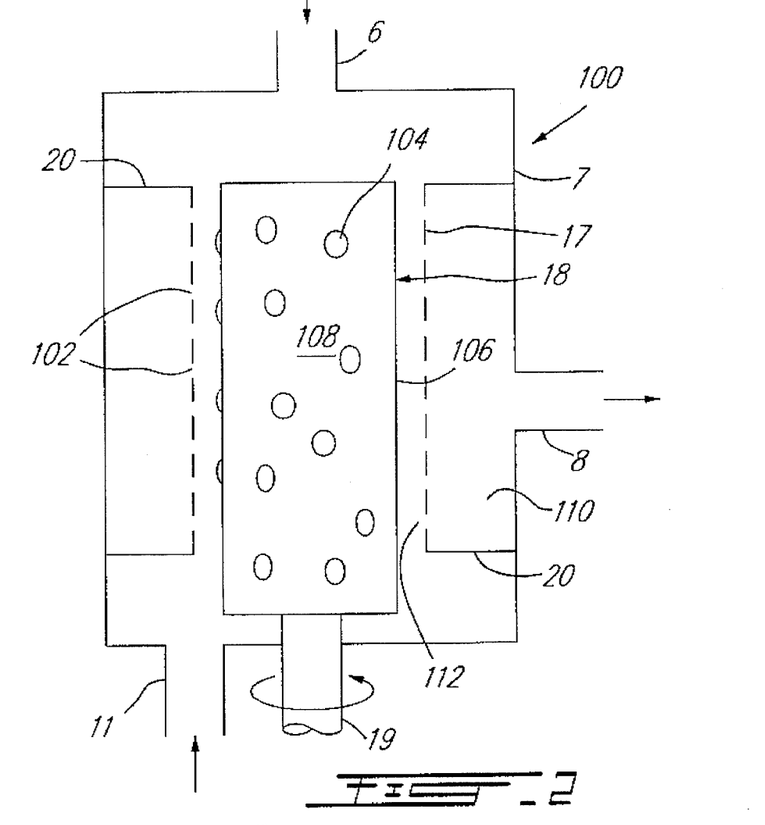
FIG. 2 is a schematic sectional view of an embodiment of the analytic screen device according to the invention, in which half of the outer shell has been omitted to show the screen plate, rotor and interior features.
Figure 3:
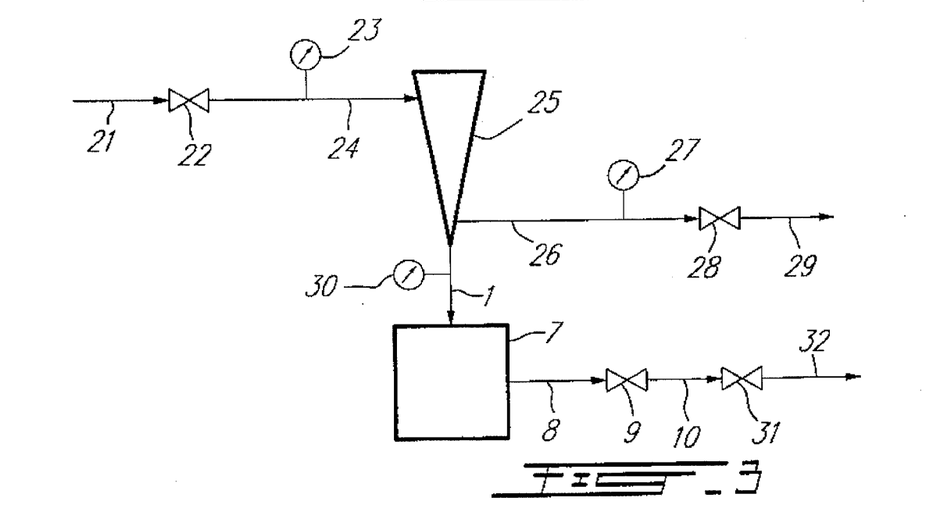
FIG. 3 is a schematic elevation view of a hydraulic system according to the invention.

The apparatus of the invention for measuring contaminant levels in a pulp suspension is comprised of two main components, an analytic screen, as illustrated in FIGS. 1 and 2 and the associated hydraulic system of FIG. 3.

An analytic screen according to the invention will be explained with reference to FIGS. 1 and 2. FIG. 1 shows a schematic elevation view of a preferred embodiment of the analytic screen 100 of the invention. FIG. 2 shows a sectional view of the analytic screen 100.

The analytic screen 100 comprises a vessel housing 7 which contains a cylindrical screen plate 17 having apertures 102 and a screen rotor 18. The preferred geometry of the apertures 102 in the screen plate 17 is slots, but holes or other geometrical shapes may also be used. The essential requirement is that the size of the apertures 102 is chosen to be a barrier to the oversize contaminants, but to permit passage of the pulp fibres. The rotor 18 in the preferred embodiment has a cylindrical core 106 with appendages 104 on its outer surface 108 to induce pressure pulsations at the surface of the screen plate 17 which are sufficient to backflush and clear the screen plate apertures. Alternate designs of the rotor 18 may use a hollow core with foil set near screen plate 17, or have the rotor 18 positioned on the discharge side of the screen plate 17.

Furthermore, the appendages 104 may take different forms, for example, they may be bumps or protuberances, rotors with long blades set parallel to the axis of rotation of rotor 18, or rotors with a shaped core, for example, a lobed cross-section.

The rotor 18 is powered by a shaft drive 19 which is, in turn, powered by a belt drive and motor (not shown) in the preferred embodiment.

Opposed upper and lower annular walls 20 define with the cylindrical screen plate 17 an annular chamber 110 through which pulp liquid and fibres pass to discharge fitting 8.

An annular zone 112 is defined between screen plate 17 and rotor 18. Zone 112 serves as a collection zone in which contaminants are isolated.

The detection system operates in one of three modes. In the "detection mode", a suspension of contaminants and residual pulp passes from the centrifugal concentrator 25 to the screen inlet line 1, through the inlet/flush three-way valve 2, line 4, and inlet/purge three-way valve 5, to the screen inlet fitting 6 and vessel housing 7. The oversize contaminants are retained within the zone 112, while the pulp and suspension passes from zone 112 through apertures 102 in screen plate 17 to chamber 110 and thence through the discharge fitting 8, and are returned through the discharge line 10 to the process stream or sent to sewer.

In the "flush mode", the inlet/flush three-way valve 2 is repositioned to stop the flow from the centrifugal concentrator 25 and initiate a flow of fresh water from line 3, and through to the screen inlet fitting 6. This flow passes through the screen plate 17 and through to the discharge line 10. At the same time, the flush line valve 12 is opened to allow a second flow of fresh water to pass from line 13 through the flush fitting 11 and through the screen plate 17. The combination of the two flows of fresh water is to cause any residual fibre to pass from the zone 112 through screen plate 17, so that only the collected oversize contaminants remain in the zone 112.

In the "collection mode", the inlet/purge three-way valve 5 is repositioned to connect the screen inlet fitting 6 with the contaminant collection line 14. The flush line valve 12 remains positioned to pass flush water to the vessel housing 7. Thus the plastic contaminants that have been retained within the zone 112 during the detection and flush modes will pass through the screen inlet fitting 6 through the inlet/purge three-way valve 5 and contaminant collection line 14, to the contaminant receptacle 15. The contaminant receptacle has a mesh 109 on its lower surface, with the mesh size chosen to retain the contaminants, but to pass the flush water through the contaminant drainage line 16 to sewer. The contaminants removed from zone 112 are substantially free of pulp fibres which would interfere with the subsequent measurement.

Surprisingly it is found that the operation of the method, and in particular the mechanical action of the rotor to which the contaminants are subjected, does not result in disintegration of the oversize particles into smaller particles.

Measurement of the level of contaminants is based on the successive operation of the "detection", "flush", and "collection" modes. In the preferred embodiment of the system, an electrical control unit is used to automatically adjust the valve positions after prescribed time intervals, and thus switch from one mode to the next. The duration of the detection mode is typically in the order of hours, while the durations of the flush and collection modes are in the order of minutes. At the end of the collection mode, the contaminants are manually removed from the contaminant receptacle for measurement and analysis. When the system is operated in its usual, continuous fashion, another cycle of operating modes would follow upon the completion of the collection mode.

The hydraulic system according to the invention will be explained with reference to FIG. 3. FIG. 3 shows a schematic elevation view of the hydraulic system.

The hydraulic system includes a sampling line 21 which draws a sample of the pulp suspension to be assessed from a process line or stirred vessel. The sample flow then passes through the sample line valve 22 and centrifugal concentrator feed line 24 to the centrifugal concentrator 25. The flow from the centrifugal concentrator feed line 24 passes into the centrifugal concentrator 25 and is divided into two streams, one of which contains an elevated concentration of contaminants. The stream with the reduced concentration of contaminants passes through the centrifugal concentrator accept line 26 and centrifugal concentrator accept valve 28 to the process return line 29. The accept flow in line 26 is typically returned to the process to avoid the loss of fibre.

The stream leaving the centrifugal concentrator 25 with the elevated concentration of contaminants passes through the centrifugal concentrator reject line 1, and as described in greater detail in FIG. 1 and during the collection mode, goes through the screen vessel housing 7, discharge fitting 8, discharge control valve 9, discharge intervalve line 10, discharge isolation valve 31 and discharge line 32 to return to the process. During the flush and collection modes, the flow through the centrifugal concentrator reject line 1 is stopped, and the full flow from the centrifugal concentrator passes through the centrifugal concentrator accept line 26.

The efficiency of the centrifugal concentrator for concentrating contaminants is dependent on there being an appropriate flow through the centrifugal concentrator 25 to develop the centrifugal effect. The sample line valve 22, centrifugal concentrator accept valve 28 and discharge control valve 31 are adjusted to provide the appropriate flows through the concentrator 25. To guide the adjustments of these valves, pressure readings may be obtained from the sample line pressure gauge 23, centrifugal concentrator accept line pressure gauge 27, and centrifugal concentrator reject line pressure gauge 30.

The efficiency of the centrifugal concentrator 25 for concentrating contaminants is also dependent on having at appropriate reject flow through the concentrator reject line 1. This flow is assessed in the present embodiment by measuring the flow from the discharge line 10. The aforementioned pressure and flow measurements and adjustments of the control valves may be done intermittently and manually if the pressure in sample line 21 is relatively constant. Automatic flow and pressure measurements, and computer-controlled manipulation of the control valves will be required if the pressure in sample line 21 varies significantly.

To estimate the concentration of contaminants in the sample stream, one divides the number of contaminants collected in the contaminant receptacle 15 by the efficiency of the centrifugal concentrator, and the amount of pulp mass that passed through sample line 21 during the measurement period. The efficiency of the centrifugal concentrator is obtained from separate, off-line evaluations. Estimates of the pulp mass require a knowledge of pulp concentration, volumetric flow rate through the sampling line 21 and duration for which the volumetric flow rate is maintained. Pulp concentration may be estimated by manual measurements, or by on-line electromechanical devices. The volumetric flow rate may be inferred from the pressure differential between the sample line pressure gauge 23 and the centrifugal concentrator accept line gauge 27, or by using a dedicated flow meter on the sampling line 21.

In order to disclose more clearly the nature of the present invention, the following examples illustrating the invention are given.

EXAMPLES

Example 1

Detection of lightweight contaminants.

A dilute, well-dispersed suspension of bleached kraft pulp was prepared in a tank. The suspension was circulated through the analytic device 100 of FIGS. 1, 2 and 3, operated in "detection mode". The flow from the centrifugal concentrator accept line 29 and discharge line 32 were returned to the tank to enable the system to run continuously.

A pre-measured dosage of oversize, lightweight (plastic) contaminants was then prepared and injected directly into the sample line 21 using a "tee" fitting that was specially installed for this test- The system was then run in "collection" mode for a period less than 5 minutes, which is substantially less than the usual duration of this mode, but sufficient in this case to allow plastic specks to move from the point of injection to the collection zone 112. The "flush " and "collection" modes then followed and the amount of contaminants collected was compared to the amount injected into the sample line 21, to yield a measure of the efficiency of the centrifugal concentrator.

Figure 4:
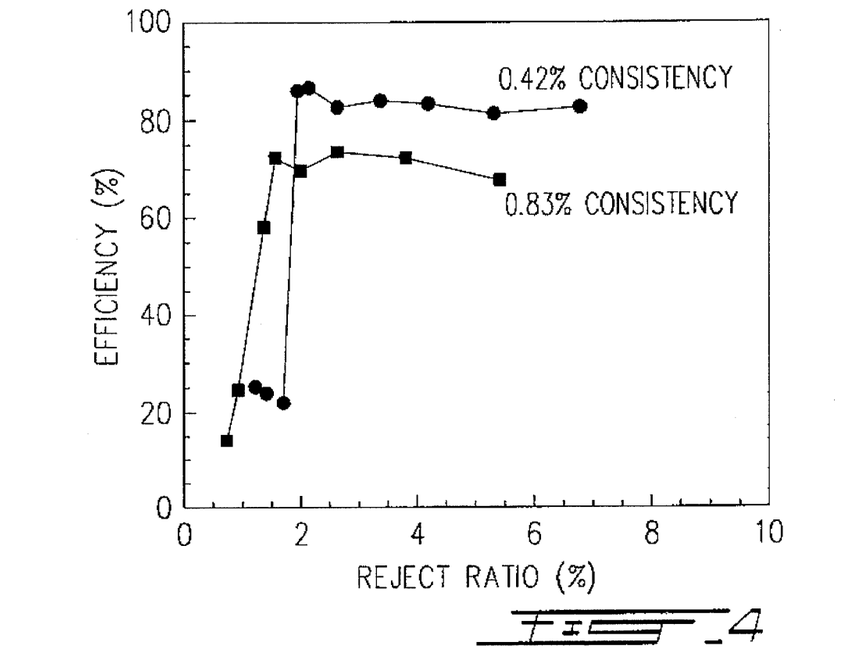
FIG. 4 presents speck capture efficiency data for the present invention which attests to its ability to remove a very high percentage of the lightweight contaminants in the flow that enters the hydraulic system.

This procedure was repeated for a range of operating conditions for the centrifugal concentrator, and most significantly for a range of reject ratios, which is the percentage of the feed flow to the centrifugal concentrator 25 that leaves as the reject flow. These tests were alternated with a control test where no contaminants were injected. The overall results of this test programme are shown in FIG. 4. These data show that: 1) high (i.e. greater than 75%) removal efficiencies may be obtained providing the reject ratio exceeds a threshold value of about 2.5%, 2) for reject ratios above this value, efficiency decreases slightly with increased reject ratio, 3) efficiency is higher at a pulp consistency of 0.42% than at a consistency of 0.83%.

Example 2

Survival of lightweight contaminants.

A second issue is whether contaminants that are retained by the screen plate 17 will be comminuted by prolonged contact with the screen rotor 18. To test this effect, a dilute, well-dispersed suspension of bleached kraft pulp was prepared in a tank. A dosage of typical, oversize contaminants was then prepared and their size distribution was measured. The dosage of contaminants was installed directly in the zone between the screen plate 17 and screen rotor 18. The suspension of pulp was circulated through the invention, with the invention operated in "detection mode". During this test, the flow from the centrifugal concentrator accept line 29 and discharge line 32 were returned to the tank to enable the system to run continuously.

The duration of operation in "detection mode" was 24 hours, which is close to the upper limit of time that the system would be run in this mode. The usual "flush" and "collection" modes were then executed, and the contaminants were collected and their size distribution was reassessed.

Figure 5:
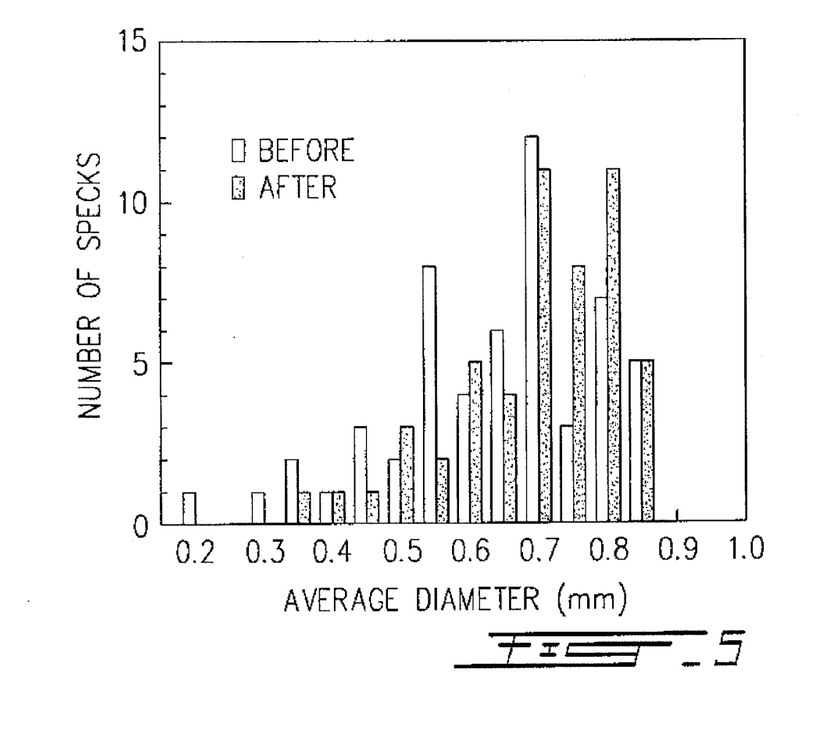
FIG. 5 presents speck counts and speck size distributions which demonstrate the ability of the analytic screen to retain specks without comminuting them.

FIG. 5 shows the contaminant distribution before and after their extended residence within the analytic screen. In particular, these data show that 52 of the 55 specks were recovered (95%), even with an extreme residence time within the screen. Moreover, no significant comminution (as indicated by a shift to smaller contaminant sizes) is apparent.

Example 3

Passage of pulp through the analytic screen.

A third issue is whether extended operation of the system will lead to significant accumulations of pulp fibres within the analytic screen 17. If this were to occur to a significant extent, the collected contaminants would be masked by the accumulated pulp fibres and the system would be substantially less convenient to use.

As in the previous two examples, a dilute, well-dispersed suspension of bleached kraft pulp was prepared in a tank. The analytic device 100 of FIGS. 1 to 3 was then run continuously in detection mode for a 24-hour-period, which is close to the upper limit of time that the system would be operated in this mode. As in previous examples, the flow from the centrifugal concentrator accept line 29 and discharge line 32 were returned to the tank to enable the system to run continuously. This test fairly simulated a situation where a total of over 1000 kg of pulp was sampled by the system through the sample line 21.

At the end of the period that the system was run in "detection" mode, the "flush" and "collection" modes were run. The amount of pulp that was retained in the collection receptacle 15 was less than 0.1 g (over-dry equivalent) which would present no significant impediment to making a quick and convenient measurement of any oversize contaminants collected.

The ability to efficiently pass fibre through the screen plate 17 is a reflection of the effective action of the screen rotor 18 to induce pressure pulsations which backflush the screen apertures 102 and keep them clear.

Example 4

Reliable and convenient contaminant measurement.

A full test of the performance of the process described by reference to FIGS. 1–3 was made by installing the system of FIGS. 1 to 3 in a typical application within an industrial mill which produced pulp in board form. The detection system was installed to draw a sample of pulp from the full process stream.

Day-to-day measurements of the concentration of plastic contaminants were made. Consistent with the objectives of the present invention, these data provided the mill operators with an insight into the quality of their product, which was not otherwise available. Consistent with Example 3, the amount of pulp discharged into the collection receptacle was small and did not appreciably increase the time required to count the collected contaminants.

For this test period, the system was operated by automatic operation of the control valves to switch from one mode to the next. Measurements of pulp concentration were made off-line. The volumetric flow rate was measured using an on-line flow meter.

We claim:

1. A process for determining the content of oversize contaminant particles of an aqueous cellulosic pulp comprising:
   a) withdrawing a sample stream of aqueous cellulosic pulp from a mass of said pulp;
   b) separating a contaminant fraction of contaminant particles from a pulp fibre fraction, of said pulp,
   c) screening oversize contaminants in said contaminant fraction on a screen, while preventing blockage of the screen with pulp fibers and oversize contaminants of the contaminant fraction and maintaining said contaminants in a zone adjacent said screen, said screen having apertures of a size such as to be a barrier to passage of the oversize contaminants while permitting passage of an aqueous vehicle and residual pulp fibres of said contaminant fraction,
   d) recovering the oversize contaminants substantially free of pulp fibres from said zone,
   e) measuring the recovered oversized contaminants, and
   f) determining the contaminant content of said pulp from the measurement of e) in conjunction with operating parameters of steps a), b) and c).

2. A process according to claim 1, wherein said sample stream in step a) is withdrawn as a continuous stream from said mass; step b) comprises continuously centrifuging said continuous stream to produce a pulp fibre fraction and said contaminant fraction, continuously discharging said pulp fibre fraction, and continually feeding said contaminant fraction to said screen in step c).

3. A process according to claim 2, wherein step d) comprises periodically flushing the screen to remove the oversize contaminants from said zone in a flush stream, while interrupting feed of contaminant fraction in step b) to said screen in step c); and isolating the contaminants from said flush stream.

4. A process according to claim 3, including determining the amount of sample stream which provided the contaminants measured in step d) and the efficiency of the centrifuging as operating parameters of steps a), b) and c) for the determination in step f).

5. A process according to claim 4, wherein said contaminants comprise plastic particles.

6. A process according to claim 5, wherein step c) comprises flowing said contaminant fraction from step b)

into said zone adjacent said screen and inducing pressure pulsations in said zone effective to prevent blockage of the screen with the pulp fibers and the contaminants and maintain the contaminants in said zone.

7. A process according to claim 6, wherein said zone is an annular zone defined between said screen and a rotor, said screen comprising a cylindrical tubular wall having said apertures therein, said rotor being spaced from and surrounded by said tubular wall, said zone being an annular zone between said rotor and said tubular wall, and comprising rotating said rotor to induce said pressure pulsations.

8. An apparatus for isolating the contaminant content of an aqueous cellulosic pulp to permit determination of such content comprising:

i) a separating unit for separating a sample stream of an aqueous cellulosic pulp into a contaminant fraction and a fibre fraction; said separating unit have an inlet for flow into the unit of the sample stream, a first outlet for the fibre fraction and a second outlet for the contaminant fraction, ii) a screening unit in flow communication with said second outlet via a first line, and including a screen and means to induce pressure pulsations in a zone adjacent said screen effective to prevent blockage of the screen and maintain the contaminants in said zone, said screen having apertures of a size such as to be a barrier to passage of oversize contaminants in the contaminant fraction while permitting passage of an aqueous vehicle and residual pulp fibres of the contaminant fraction, and discharge means for discharge of the residual pulp fibers, iii) a flushing line communicating with said screening unit for flow of flushing liquid to said zone, iv) a second line in flow communication with said screening unit for flow of flushing liquid with oversize contaminants from said zone, v) a collecting unit for contaminants in flow communication with said second line, vi) a first valve associated with said first line adjustable between open and closed positions to allow and prevent flow of the contaminant fraction from said separating unit to said screening unit, vii) a second valve associated with said flushing line adjustable between open and closed positions to allow and prevent flow of flushing liquid to said screening unit, and viii) a third valve associated with said second line adjustable between open and closed positions to allow and prevent flow of flushing liquid and contaminants from said zone of said screening unit to said collecting unit.

9. An apparatus according to claim 8, in which said separating unit is a centrifugal separator.

10. An apparatus according to claim 8, in which said means to induce pressure pulsations comprises a rotor and second screen comprises a cylindrical, tubular wall having said apertures therein, said rotor being disposed within and spaced apart from said tubular wall, said zone being an annular zone defined between said screen and said rotor.

11. An apparatus according to claim 10, further including a third outlet in said screening unit in flow communication with a downstream side of said screen.

12. An apparatus according to claim 11, wherein said rotor has a cylindrical body and appendages on said body adapted to induce pressure pulsations in said annular zone.

13. An apparatus according to claim 8, further including a second flushing line communicating with said zone of said screening unit and a fourth valve associated with said second flushing line, adjustable between open and closed positions to allow and prevent flow of flushing liquid to said zone of said screen unit.

* * * * *